United States Patent [19]

Sinor et al.

[11] 4,169,128
[45] Sep. 25, 1979

[54] COAL LIQUEFACTION APPARATUS

[75] Inventors: Jerry E. Sinor, Longmont, Colo.; James A. Gray, Newbury Park; Carl L. Oberg, Canoga Park, both of Calif.

[73] Assignee: Rockwell International Corporation, El Segundo, Calif.

[21] Appl. No.: 771,484

[22] Filed: Feb. 24, 1977

Related U.S. Application Data

[63] Continuation-in-part of Ser. No. 689,002, Apr. 24, 1976.

[51] Int. Cl.² .............. B01J 8/08; C10G 1/06; H01C 3/08; H05B 3/40
[52] U.S. Cl. .................... 422/224; 48/77; 165/DIG. 5; 208/8 R; 219/523; 338/218; 422/199; 422/202; 422/232; 422/310
[58] Field of Search .............. 23/284, 277 R, 259.5; 48/197 R, DIG. 4, 210, 77, 101; 110/22 A; 260/679 A; 201/31, 32; 208/8, 10, 58; 422/199, 202 (U.S. only), 224, 232 (U.S. only), 310 (U.S. only); 338/218; 165/DIG. 5

[56] References Cited

U.S. PATENT DOCUMENTS

| 2,679,544 | 5/1954 | Bills ................... 260/679 |
| 2,713,601 | 7/1955 | Bills ................... 260/679 R |
| 3,048,476 | 8/1962 | Dwyer ................. 23/284 |
| 3,737,285 | 6/1973 | Hicks, Jr. ............. 23/277 R |

Primary Examiner—Joseph Scovronek
Attorney, Agent, or Firm—L. Lee Humphries; Henry Kolin; Clark E. DeLarvin

[57] ABSTRACT

Disclosure is made of an apparatus for reacting carbonaceous material with heated hydrogen to form hydrocarbon gases and liquids suitable for conversion to fuels wherein the reaction involves injection of carbonaceous material such as pulverized coal entrained in a minimum amount of gas and mixing the entrained coal at near ambient temperature with a separate source of heated hydrogen. The hydrogen is heated in a coil having an increasing inside diameter. The heated hydrogen and entrained coal are injected through a rocket engine type injector device. The coal particles are reacted with hydrogen in a reaction chamber downstream of the injector. The products of reaction are rapidly quenched as they exit the reaction chamber and are subsequently collected.

3 Claims, 8 Drawing Figures

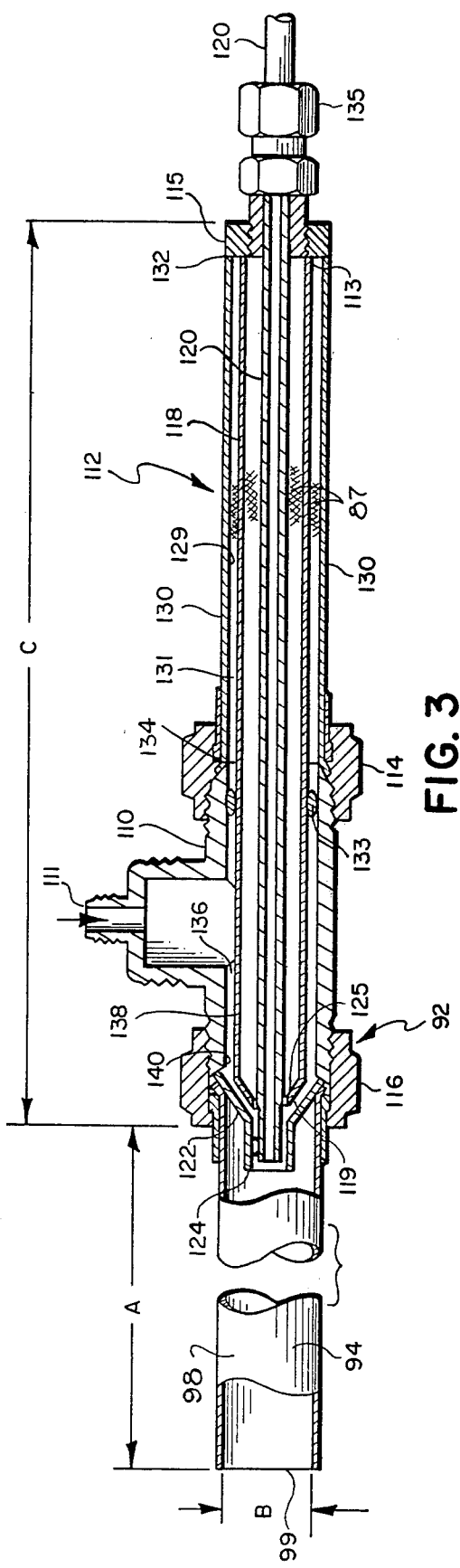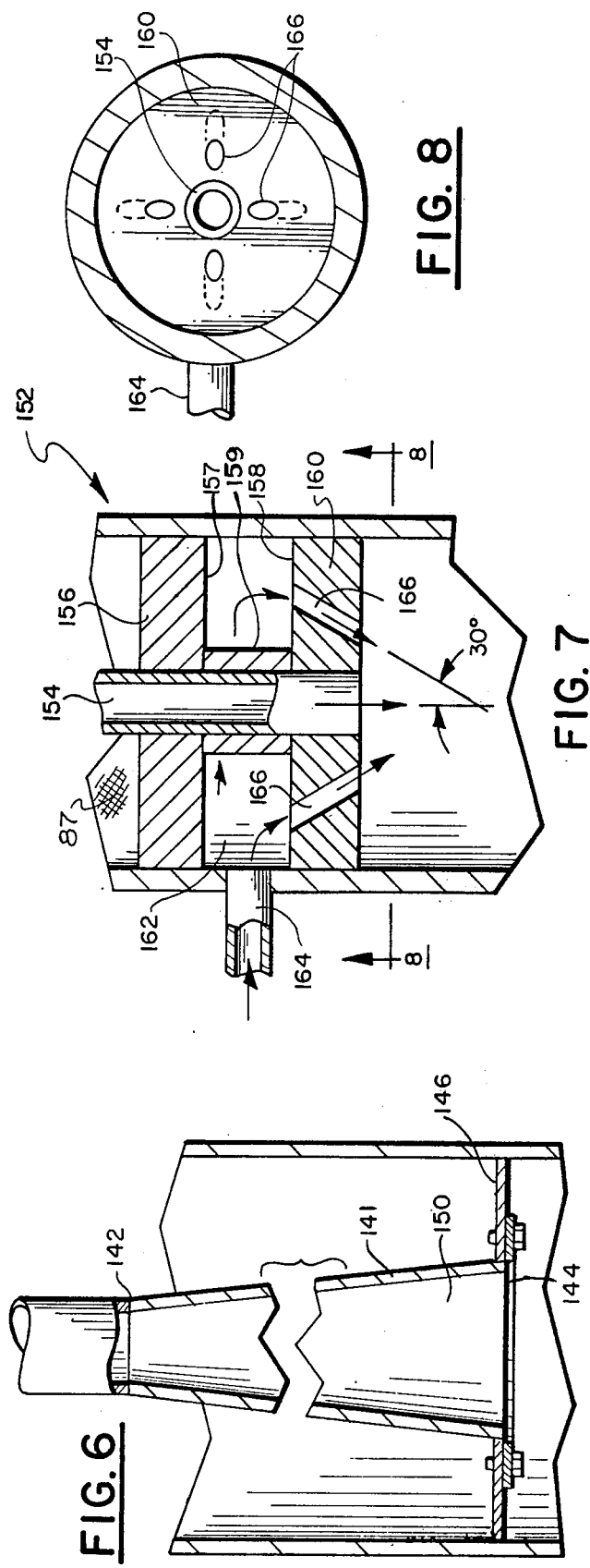

COAL LIQUEFACTION APPARATUS

CROSS-REFERENCE TO RELATED APPLICATIONS

This application is a continuation-in-part of application Ser. No. 689,002 filed May 24, 1976.

BACKGROUND OF THE INVENTION

1. Field of the Invention

This invention relates to the field of coal conversion to form hydrocarbon liquids suitable for conversion to fuels.

More particularly, this invention relates to an apparatus for reacting pulverized coal with heated hydrogen to form hydrocarbon liquids suitable for conversion to fuels or for use as a chemical feedstock.

2. Description of the Prior Art

The problem is to react coal directly with hydrogen in such a way as to maximize the yield of liquid products. A number of researchers have shown that at the beginning of coal pyrolysis a transient period exists for a few tenths of a second where the coal is highly reactive toward hydrogen. If excess hydrogen is not available during this period, some of the free-radical pyrolytic fragments will strip molecular hydrogen from the aromatic groups while other fragments will polymerize to form unreactive char. The overall effect is a limited yield of liquid and gaseous hydrocarbons, and a large yield of char. If instead, excess hydrogen is present during the critical transient period, many more hydrogenated fragments that are amenable to still further hydrogenation are produced. The overall effect of pyrolysis in hydrogen is a much larger yield of liquids and gases, and a lower char yield.

It is generally well known the conversion of coal to liquid or gaseous fuels is achieved by the addition of hydrogen. This may be accomplished by the direct contact of coal with hydrogen as in the Bureau of Mines Hydrane process to produce methane; by a catalyzed liquid-phase reaction with hydrogen to produce liquid products as in the Synthoil process; or indirectly by reacting coal with steam. Many different processes have been proposed and are under development. These schemes vary in the method of contacting coal and hydrogen or steam, and in the type of coal feed utilized. A solid such as coal can be contacted with a gas in three basically different ways. In the first, gas is forced through a fixed or slowly moving bed of solid. Another method of contact is by use of a fluidized bed. With sufficiently small solid particles and a sufficiently high gas velocity in vertical upward flow the air dynamic drag forces on the individual particles begin to approach the gravitational forces and the particles themselves begin to move about. The bulk properties of the gas solid mixture then become those of a fluid. Because of the improved heat and mass transfer characteristics in a fluidized bed as opposed to a fixed bed, most coal gasification processes now are the fluidized bed variety. Yet another basic category of gas solid contacting is entrained flow as in the Bigas process. In this regime gas velocities are high enough and particle sizes low enough that the solid particles are carried along with the gas stream. An advantage of the entrained flow processes is the ability to utilize any grade or class of coal. Caking coals will agglomerate causing difficult problems when fed to fluidized or fixed bed systems. Further advantages of entrained flow with respect to gas production include operation at high temperatures so that tar production is kept to a minimum, adaptability to slagging conditions and high energy production per unit volume. The present invention utilizes this type of entrained flow coal conversion process. Heretofore no large scale attempt to use this approach for direct hydrogenation of coal has been made.

A patent issued to W. C. Schroeder, U.S. Pat. No. 3,030,297, describes a process which comprises heating dry particles of coal entrained in a heated stream of hydrogen at total pressure of about 500–6000 psig from a temperature below about 300° C. to a reaction temperature in the range of from about 600° C. to about 1000° C. Two minutes are required to heat the coal particles to about 600° C. and then two to twenty seconds time at temperature for hydrogenation. The slow heat-up results from the main hydrogen stream being utilized to carry the coal into the reactor. The products of reaction are then cooled below reaction temperature to provide a product comprised of light oil, predominantly aromatic in nature, and hydrocarbon gases, primarily methane and ethane, and carbon monoxide.

This process is disadvantaged in that the coal particles entrained in the hydrogen are preheated prior to introduction into a heating chamber thus the reaction process is started upstream of the reaction chamber which will cause agglomeration and plugging within the conduit carrying the entrained coal. The present invention overcomes this agglomeration problem by providing two sources of gas, one source of gas such as hydrogen brings entrained coal into an injector at a temperature substantially less than the coal reaction temperature, and a separate source provides heated hydrogen to an injector which contacts the entrained dense phase coal downstream of an injector within a reaction zone thereby starting the hydrogenation process within the reaction chamber and not upstream of the chamber.

Schroeder is further disadvantaged in that he attempts to heat the entrained coal particles through a tube wall. At the mass throughputs specified in the example, it is doubtful that enough heat could be transferred through the tube wall in a reasonable length to sufficiently heat the coal and, at the same time, use the tube wall to contain the system pressure. This type of reactor does not scale to the necessary larger diameters for commercial coal conversion reasonably because the heat transfer surface-to-volume ratio decreases rapidly with an increase in size.

Schroeder is still further disadvantaged in that the mixing and the heating takes place in minutes and seconds whereas the present invention accomplishes the hydrogenation of the entrained coal in milliseconds and if a uniform flow pattern can be maintained (to avoid back mixing which will cause longer residence time and gas production instead of liquids) and if the coal can be dispersed uniformly even on a microscopic scale (to minimize gas diffusion limitations), and if rapid and efficient quenching can be achieved (Schroeder carries the hydrogenated products through a conduit towards a separate quenching chamber whereas the present invention quenches the reaction products immediately upon exiting the end of the reaction chamber), then it should be possible to hydrogenate a substantial fraction of the coal to liquid products. The utilization of rocket engine type injector principles in a coal liquefaction plant as described in the present invention is believed to be unique and is one of the principal objects of the invention.

Another patent issued to Schroeder, et al., U.S. Pat. No. 3,152,063, teaches a process which comprises dispersing pulverized and catalyzed coal, in the absence of a pasting oil, in hydrogen under a pressure of about 500 to 4000 psig, reacting the mixture of coal and hydrogen at a temperature in the range of about 450° C. to 600° C., for a gas residence time of less than about 200 seconds, cooling the reaction products and recovering liquid and gas hydrocarbon products therefrom.

Schroeder teaches passing of catalyzed coal and hydrogen into a two-stage reactor that consists of a multiplicity of parallel tubes axially extending within the reactor. The tubes are heated by a source of hot gas to start the reaction within the tubes. Vaporized oil and gas products are drawn off as well as unused hydrogen to a cooling device. The residual heavier oil and tar products are collected in the bottom of the reactor and a source of hydrogen may then be brought in to further hydrogenate these heavier products.

This invention is disadvantaged in that the pulverized coal must be passed through a catalyzing process, sent through a dryer and grinder and finally separated into minute particles by passing the coal through a screening process. The present invention utilizes finely-divided pulverized coal directly without the foregoing pretreatment process.

Schroeder's invention is further disadvantaged in that it also utilizes the carrier hydrogen in the coal passages as the main source of hydrogen. The heat-up process then takes considerable time as compared to the present invention in that the carrier gas cannot be pre-heated prior to entering into a reaction chamber.

Additionally, the invention is disadvantaged in that the coal particles are heated through a tube or a series of tubes thereby seriously affecting the ability to scale-up the process to commercial production proportions. A commercial unit would necessarily have to process in the neighborhood of 1000 tons/hour. The Schroeder patents teach a mass throughput of approximately 145 lbs/hr ft.$^2$, a very low process rate. For example, in a commercial reactor using the Schroeder process, each reactor being 15 feet in diameter, 82 reactors would be needed to process 1000 tons/hr of coal. In addition, because of the small surface-to-volume ratio the reactors would have to be on the order of one hundred feet long to transfer sufficient heat through the wall transporting the entrained coal particles. One of the most important advantages of the high throughput of dense phase coal particles through the reactor of the present invention (33,000 lbs/hr ft.$^2$) is that it is scaleable to a commercial size. Two reactors utilizing the principles set forth in the following specifications, 6-feet in diameter would process 1000 tons/hr of coal. The heat is supplied directly in the hydrogen so that vessel surface-to-volume ratio is not a limiting factor.

Although the chemistry of coal pyrolysis and hydrogenation has been apparent for some time, no well-developed reactor exists which efficiently utilizes the rapid-reaction regime. Some of the basic reasons for this appear to be a lack of adequate gas/solid injection and mixing technology, difficulty in meeting chemistry and residence time requirements, and agglomeration and plugging of the reactor. Hydrogenation of raw bituminous coal usually results in agglomeration, so that typical fluidized bed or moving bed reactors cannot be used as heretofore described. In addition, the requirement of short residence time (less than 1 sec) necessarily restricts the reactor to an entrained flow type. By maintaining rapid mixing, heat-up, and reaction of the coal near the point of injection and hot reactor walls, the agglomeration problem can be avoided. The uniform and precise mixing of extremely large feed streams in time of a few milliseconds is the special accomplishment of large rocket engine injectors and one of the principal objects of the present invention.

SUMMARY OF THE INVENTION

It is an object of this invention to convert carbonaceous material entrained in a gas in a dense phase to hydrocarbon liquids and gases by hydrogenating the coal particles.

More particularly, it is an object of this invention to utilize rocket engine injection and mixing techniques in an entrained flow reactor to rapidly mix and react a separate stream of heated hydrogen with a dense phase stream of carbonaceous material at ambient temperature to produce liquid and gaseous hydrocarbons.

It is yet another object of this invention to build and operate a high-temperature, coal liquefaction reactor which minimizes secondary oil and tar decomposition reactions by optimum control of gas-phase residence time, and prevents reactor plugging from coal agglomeration by very rapid dispersion and reaction of the coal while maintaining the internal reactor wall at high temperature.

A coal liquefaction method and apparatus to produce hydrocarbon liquids and gases by hydrogenating pulverized coal with hydrogen by flowing pulverized coal particles entrained in a gas such as hydrogen in a dense phase in a coal flow conduit at a temperature substantially less than coal reaction temperatures toward an injector adjacent to a reaction chamber and a heating means is provided for heating a separate source of hydrogen. The dense phase pulverized coal is injected through the injector into the reaction chamber followed by injecting the heated separate source of hydrogen gas through the injector into the reaction chamber and means to separate the near ambient temperature dense phase coal particles and the heated hydrogen prior to injection of the dense phase coal and the heated hydrogen into the reaction chamber to prevent premature hydrogenation of the pulverized coal. A quenching means is provided adjacent the reaction chamber to rapidly arrest the hydrogenation process at a predetermined time period when the reaction products exit the reaction chamber, and a collecting means is provided for collecting the reaction products.

The coal is fed to the reactor at nearly its bulk density so that the quantity of entrained gas is minimized, and the heated hydrogen brought in separately provides the heat source needed to raise the coal rapidly to reaction temperatures.

An entrained flow reactor using rocket engine injection and mixing techniques to react a stream of hot hydrogen with a stream of pulverized coal was designed, built, and operated. As an example only, typical reactor operating conditions were 1000 psig, 1100° F., ≈150 milliseconds residence time, and 0.36 lb $H_2$/lb coal. Approximately 19% of the coal carbon was converted to a synthetic crude oil having a boiling range of 200°–350° C. and a heating value of 15,800 BTU/lb, 9% to gas containing methane, ethane, and carbon oxides, and 3% to organic compounds in the quench water. The coal throughput rate was approximately 33,000 lbs/hr ft² reactor cross section or 11,000 lbs/hr ft³ reactor volume. The products of reaction were rapidly quenched to 220° F. in a distance of 1 ft using large flowrates of water through spray nozzles.

Thus, an advantage over the prior art is the use of rocket engine injection and mixing techniques to rapidly mix and react a stream of entrained coal with hot hydrogen to produce liquid and gaseous hydrocarbons.

Another advantage of the present invention over the prior art is the minimization of secondary oil and tar decomposition reaction by optimum control of gas-phase residence time by very rapid coal particle dispersion and reaction of the coal while maintaining the internal reactor wall at high temperature.

Yet another advantage over the prior art is the prevention of coal agglomeration upstream of the reaction chamber by transporting the entrained dense phase coal in a gas at ambient temperature.

Still another advantage over the prior art is the ability to use a carrier gas other than hydrogen for transporting the coal particles in a dense phase to the injector thus minimizing explosion hazards in the coal feed system due to hydrogen leakage to the atmosphere from moving mechanical parts such as valves, buildup of explosive mixtures of hydrogen and air in the coal containing vessels, and loss of hydrogen through venting when lock hoppers are used.

A still further advantage over the prior art is the immediate quenching of the hydrogenated coal particles as they exit the end of the reaction chamber thereby maximizing the product yield of liquid and gaseous hydrocarbons.

Another advantage over the prior art is the direct hydrogenation of coal particles in a reaction chamber as opposed to heating the exterior wall of a tube surrounding the hydrogen and coal particles contained within the tube.

The above-noted objects and advantages of the present invention will be more fully understood upon the study of the following description in conjunction with the detailed drawings.

BRIEF DESCRIPTION OF THE DRAWING

FIG. 3 is an enlarged partially cross-sectioned view of the hot hydrogen and the coal flow coupling upstream of the injector;

FIG. 6 is an alternate view of the reaction chamber illustrating diverging walls from the injector face to the exit plane of the reactor tube;

FIG. 7 is an alternate view of an injector illustrating a four-on-one injection pattern; and FIG. 8 is a view taken along lines 8—8 of FIG. 7.

DESCRIPTION OF THE PREFERRED EMBODIMENTS

Figure 1:
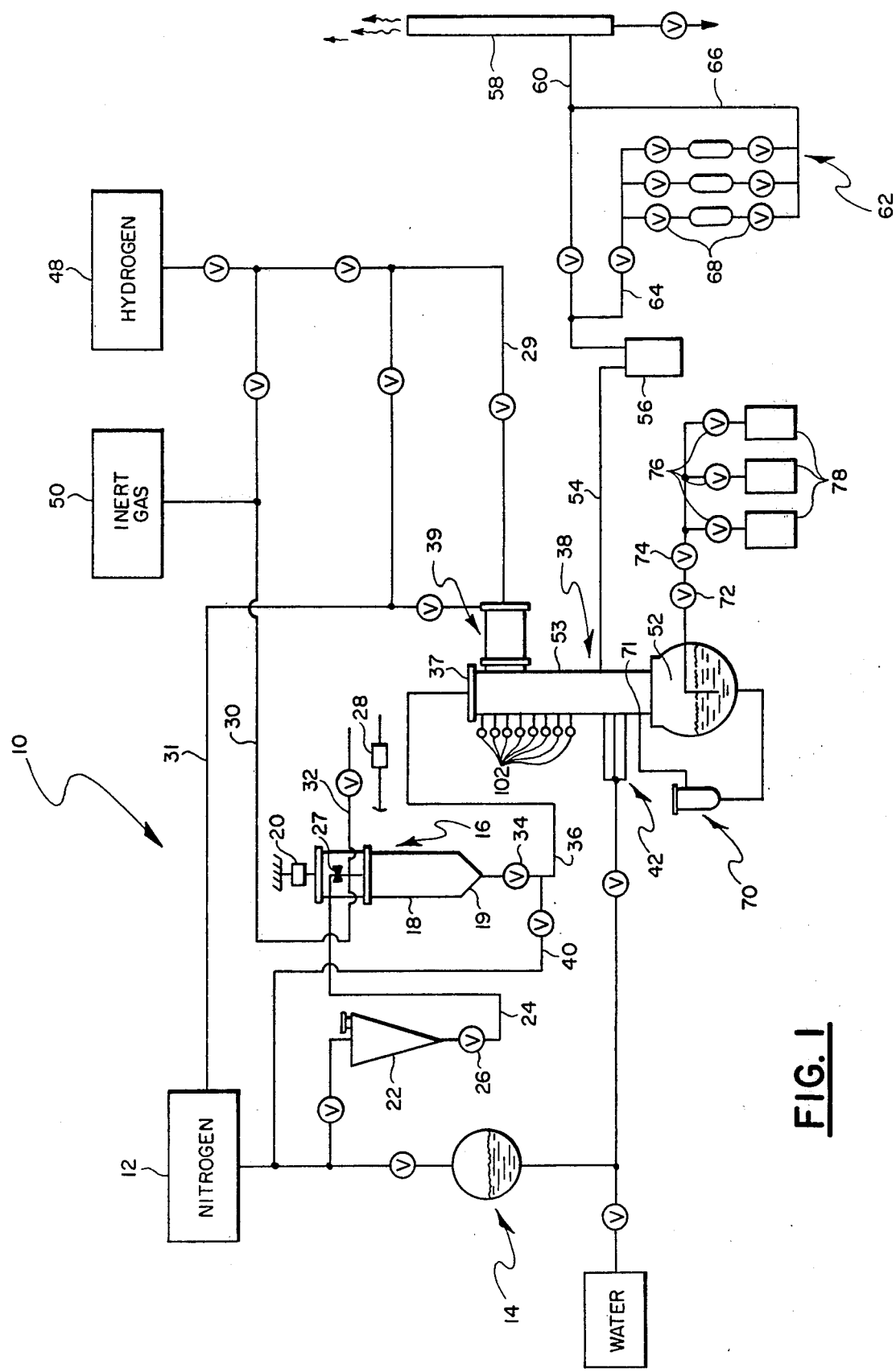
FIG. 1 is a flowsheet schematic of the coal liquefaction apparatus.

Referring now to FIG. 1, a coal liquefaction unit generally designated as 10 consists of a nitrogen supply system generally designated as 12 that serves as a purge supply source as well as a pressurizing source for a quench water tank system generally designated as 14.

Figure 4:
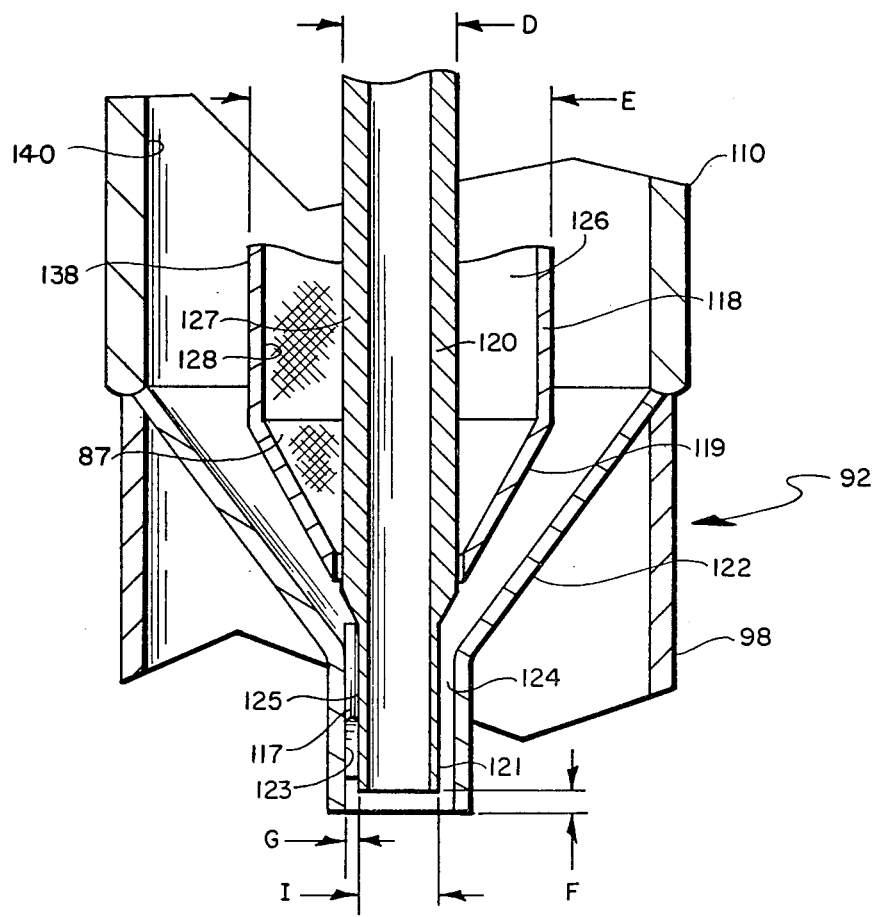
FIG. 4 is an enlarged cross-section of the concentric injector.

A high pressure coal feeder generally designated as 16 comprises a cylindrical vessel 18 suspended from a load cell 20. The coal feeder 16 is charged by flowing coal from a low pressure conical tank 22 through a tube 24. To charge the high pressure coal feeder 16, the conical tank 22 is pressurized to about 55 psig with nitrogen from supply system 12, a ball valve 26 at the conical tank bottom is quickly opened wide, and the coal flows in a dense phase through the tube 24 to the coal feeder 16. The excess nitrogen vents out of the coal feeder through a dust filter 28. After the coal feeder 16 is charged, the tube 24 is disconnected and capped as shown at 27, and the dust filter 28 is disconnected and the pressure relief line 32 connected in its place, as shown in FIG. 1. A hopper hydrogen feed line 30 from a hydrogen source 48 or inert gas from an inert gas source 50 is opened for subsequent operation. Load cell 20 readings before and after charging indicate the quantity of coal in the feeder. The bottom 19 of the coal feeder 16 is conically shaped with a 30° included angle to provide smooth discharging of coal. Coal is fed to the reactor assembly by opening a ball valve 34 and flowing in a dense phase through a feed line 36. The hydrogen or inert gas pressure in the coal feeder is maintained, for example, about 60 to 70 psi higher than in the reactor assembly generally designated as 38 so as to provide the driving force for feeding the coal to the reactor assembly 38. The weight of hydrogen carried in the coal as a percent of the coal flowrate is about 0.5% when the reaction chamber pressure is 1000 psig. In the case of inert transport gas, the weight percent transport gas will vary according to gas density. The flowrate of coal is about 0.15 pound per second and the flowrate of hydrogen is about 0.0075 pound per second where hydrogen is used as the carrier gas. Load cell readings are printed during a test so that the coal feed rate can be continuously monitored (not shown). When the feeder ball valve 34 is in a closed position, nitrogen from nitrogen supply system 12 flowing through a line 40 is purged through the feed line 36 to keep it clear and to prevent the coal side of the injector (FIG. 4) from overheating. The portion of the coal feed line passing through a top flange 37 and making up part of an injector assembly 92 (FIG. 3) is typically fabricated from stainless steel. Details of the injector assembly 92 are shown in FIGS. 3 and 4.

Pressurized water for a quench system generally designated as 42 is supplied by, for example, a 150 gallon pressurized quench water tank system 14. The flow of water can be accurately measured continuously during tests and is varied by changing the pressure on the water tank from nitrogen supply system 12. Accurate flow control is possible because the pressure drop across spray nozzles 106 (FIG. 2) is normally about 180 psi. In addition, there is about another 130 psi in pressure drop ahead of the spray nozzles.

It would be obvious to use fluid other than water to quench the hydrogenated products as they exit the reaction chamber such as steam, oil or cold gas (hydrogen).

There are three gas supply systems, one for nitrogen, one for hydrogen and one for an inert gas. The nitrogen supply system 12 supplies the nitrogen bleed to a preheater assembly 39 through a conduit 31 and reactor pressure shells 53, and for purging the coal feed line through line 40. The flows are controlled by using sonic nozzles (not shown) and varying the pressure upstream of the nozzles to obtain various flowrates. The hydrogen source 48 supplies the high pressure coal feed 16 and the preheater assembly 39. The hydrogen flow to the coal feeder 16 is on demand and is only measured with an orifice (not shown). The gas supplied to the coal feeder 16 need not be hydrogen from hydrogen source 48 but may be an inert gas such as nitrogen, carbon dioxide or mixture thereof from inert gas source 50. The hydrogen flow to the preheater assembly 39 is controlled by a sonic nozzle and upstream pressure regulator (not shown). The hydrogen system may be set up so that nitrogen can be used in place of hydrogen for purging and leak checks (not shown).

Product gas from a spherical catch tank 52 flows through a conduit 54 to a liquid separator tank 56 and then through a back pressure regulator system. After the product gas is let down in pressure, the flowrate is measured using an orifice and then the gas goes to a burnstack 58 through a tube 60. A gas sample bottle system generally designated as 62 is connected to the high pressure side through a line 64 of the gas sample bottle system 62 and is vented back into the system through a line 66 to burnstack 58. The sample bottle valves 68 are automated to open in sequence about every 30 to 60 seconds during a test.

The liquid product letdown is controlled by a tank liquid level control system generally designated as 70 that actuates an on-off valve 72. The flow out of catch tank 52 is regulated by a linear plug valve 74. The linear plug valve 74 is basically a variable orifice that is used to prevent the liquid from surging out of catch tank 52 so fast that pressure control in the reactor assembly 38 is upset. A header of three valves 76 is used to select which of drums 78 is to receive the liquid product.

Figure 2:
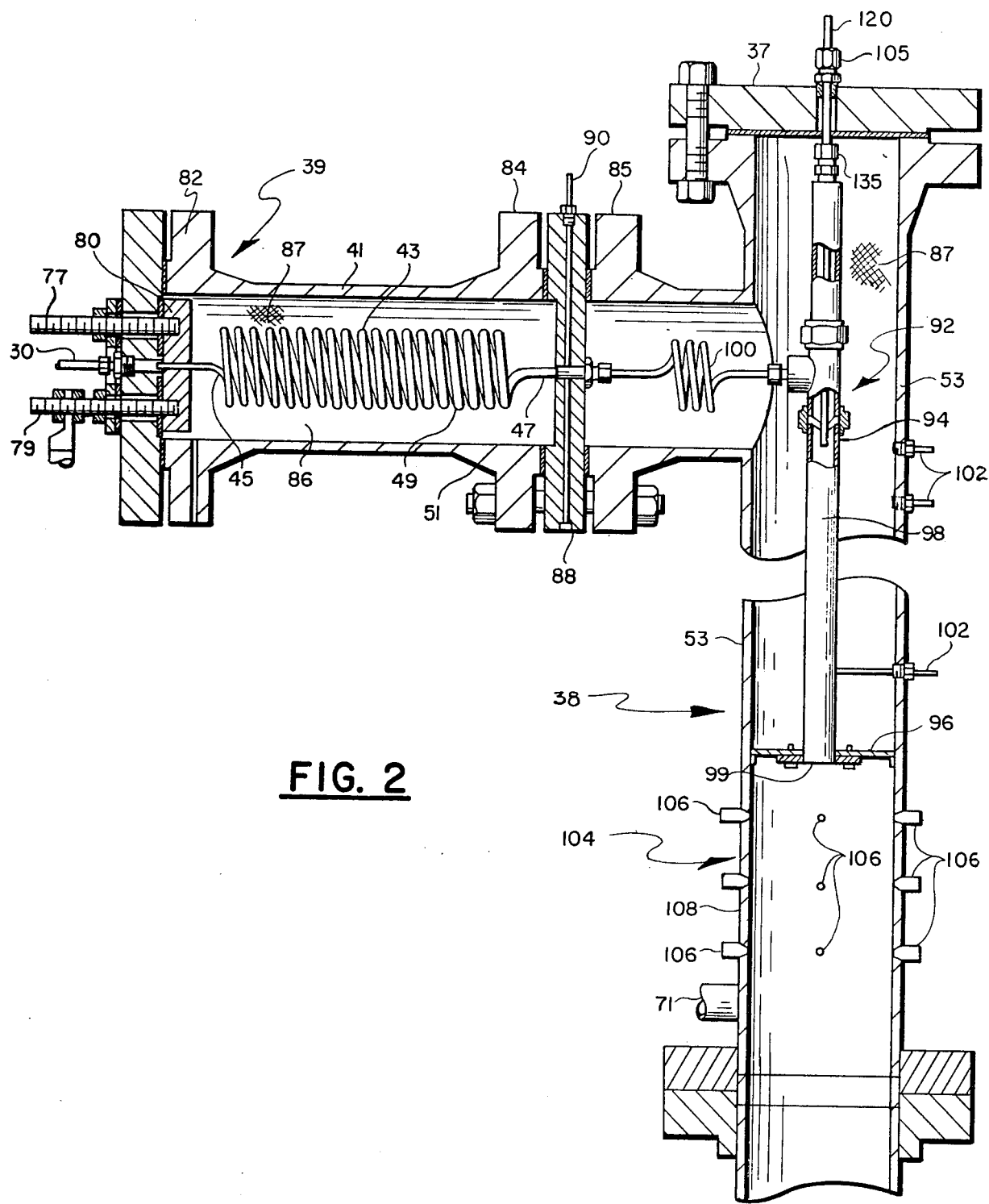
FIG. 2 is a detailed cross-section of the principal elements of the invention.
Figure 5:
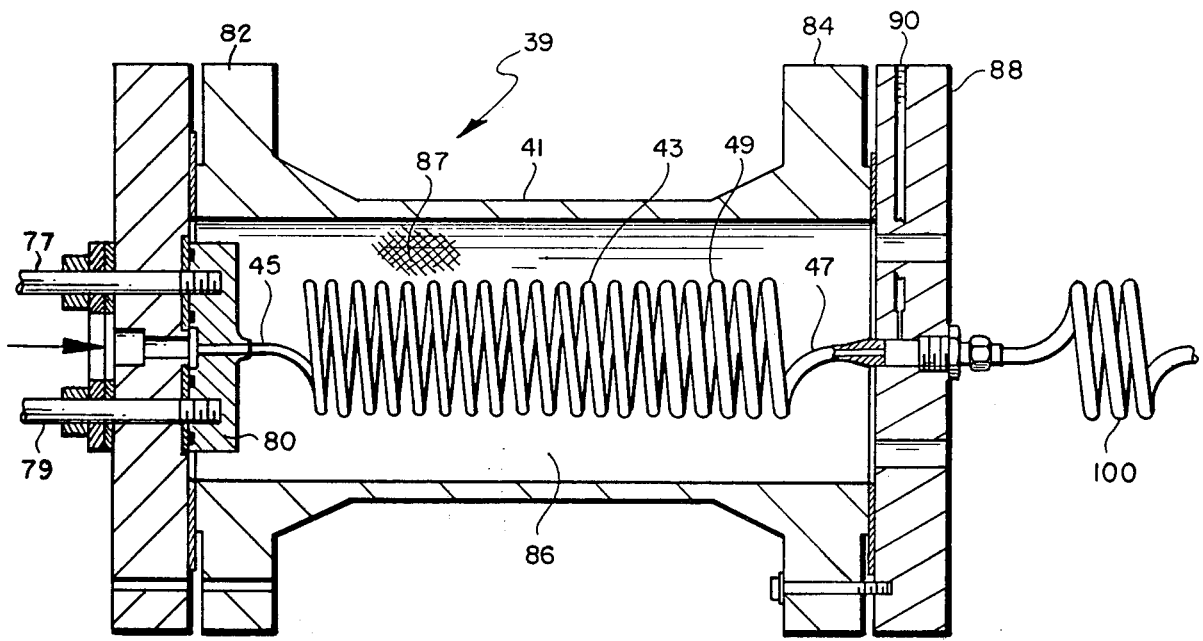
FIG. 5 is a view of the heater coil element and electrical coupling adjacent the reaction chamber and coal flow tubes.

A more detailed drawing of the hydrogen preheater assembly generally designated as 39 is presented in FIGS. 2 and 5 and of the reactor assembly generally designated as 38 is presented in FIG. 2. The hydrogen preheater assembly is contained within a pressure shell 41 and the preheater coil 43 is a stainless steel tube through which an electric current is passed as hydrogen passes through it. The preheater coil 43 is thin walled and small in diameter at end 45 and heavy walled and larger in diameter at end 47. As the hydrogen enters end 45 it is relatively cool and as it progresses down through helical-shaped preheater coil 43 it heats up and expands. The variable I.D. and wall thickness of the coil compensates for this expansion of hydrogen. Seven motor-generator sets (not shown) supply about 600-800 amps to copper stud conductors 77 and 79 connected to plate 80 through the wall 49 with a power input up to 150 Kw. The heat transfer from the resistively-heated wall 49 to the pressurized hydrogen entering end 45 of preheater coil 43 through hydrogen feed line 30 is excellent and has demonstrated efficiencies of about 99%. Since the tube wall strength is very low at the heater operating temperatures (the wall is about 200° F. hotter than the hydrogen at the exit 47 of the tube 43), the preheater coil 43 is contained in a pressure shell 41 made from, for example, carbon-steel pipe and 600 lb flanges 82 and 84. The void space 86 in the pressure shell 41 is stuffed with, for example, a very low thermal conductivity insulation 87 such as Fibrefrax, a product of Carborundum Corporation, Refractories and Insulation Division, Fibrefrax Branch, Niagra Falls, New York, and is purged continuously with about 5 SCFM of nitrogen at about 1000 psig. The copper stud conductors 77 and 79, plate 80, and inlet end 45 of the preheater coil 43 are electrically isolated from the pressure shell 41 and serve as the positive connection to the motor generator sets. The ground connection is made to another end 51 of the pressure shell 41 through the blind stainless steel flange 88 that is sandwiched between the two carbon steel, weld-neck flanges 84 and 85. A thermocouple 90 is immersed in the gas exiting the preheater assembly 39, and a pressure transducer (not shown) is connected to a similar port in the flange.

In a similar fashion, referring to FIG. 2, the reactor tube 98 and injector assembly generally designated as 92 are enclosed in a pressure shell 53 so that the hot reactor tube walls 94 experience very little stress while at high temperature. The reactor tube 98 is supported by the insulation 87 and slip fits through a hole in the insulation support plate 96 so that thermal elongation of the reactor tube 98 is allowed. The preheater assembly 39 is connected to the injector assembly 92 via a stainless steel coiled tube 100. This tube is coiled so that it can thermally elongate without applying a force against the injector assembly 92, possibly bowing the reactor tube 98. The reactor tube 98 and injector assembly 92 can easily be removed from the pressure shell 53 by removing the top flange 37 and a small amount of insulation 87. Several bosses 102 along the side of the pressure shell 53 permit thermocouple measurements along the reactor outside wall, and one directly inside the bottom of the reactor tube 98 near exit plane 99.

The quench zone 104 consists, for example, of 3 rows of 4 full-cone spray nozzles 106 that screw into the quench zone pipe wall 108 from the outside. As the reaction tube products exit the reactor 98, they are quenched immediately with water sprays supplying water at about 3 to 6 gpm. Enough spray water is used to reduce the product temperature to about 200° F. The liquid, gas, and solids are forced down into spherical catch tank 52 (FIG. 1) where the gas separates and exits. The liquid level control system 70 (FIG. 1) is used to maintain a liquid level in the spherical catch tank 52 and to let down the slurry product into drums 78 (FIG. 1). Vent line 71 connects to the liquid level control system 70.

FIGS. 3 and 4 illustrate in more detail the injector assembly 92 and reactor tube 98 combination wherein a stream of hot (1500°-2000° F.) hydrogen is reacted with a stream of pulverized coal. The injector assembly generally designated as 92, for example, consists of a housing body 110 that is separable from a coal feed line assembly 112 and the reactor tube 98 by a pair of, for example, AN type nuts 114 and 116. The coal feed line assembly 112 consists of 3 tubes, an outer shell tube 130, an insulation tube 118, and a post tube 120. The post tube 120 is ⅜ inch O.D. (Dimension "D" FIG. 4)×0.083 inch wall, 321 stainless steel. A 0.55 inch length of end 121 of the post tube 120 is machined to form end 121 to 0.254 inch O.D. (Dimension "I" FIG. 4)×0.020 inch wall. The entire injector assembly 92 is contained within the pressure shell 53 (FIG. 2). The post tube 120 extends through top flange 37 via a packing gland fitting such as a ⅜ inch Conax fitting 105 made by Conax Corporation of Buffalo, New York, and is coupled with coal feed line 36 outside of the pressure shell 53. End 121 of the post tube 120 extends concentrically within a separate cone 122 that is connected to housing body 110 by AN nut 116. An annulus 124 (FIG. 4) is defined between inner wall 123 of cone 122 and outer surface 125 of end 121 of post tube 120. Annulus 124 is 0.350 inch O.D. with a gap of 0.048 inches (Dimension "G" FIG. 4) to the outer surface 125 of end 121 of the post tube 120. End 121 is recessed 0.212 inch (Dimension "F"). Three wire spacers 117 are brazed to end 121 to center the post tube 120 and end 121 in the annulus 124. The post tube 120 is supported as it passes through a plate 115 by a ⅜ inch Conax fitting 135 that is screwed into plate 115. The insulation tube 118 is 1 inch O.D.×0.049 inch wall, 321 stainless steel and terminates at end 119 in a cone that diverges toward but is not affixed to the outer wall of the post tube 120 near end 121. End 113 of tube 118 is affixed to plate 115. An annulus 126 is defined by an outer surface 127 of tube 120 and an inner surface 128 of tube 118. The annulus 126 is filled with insulation material 87. The outer shell tube 130 is a structural member that houses concentric tubes 118 and 120 and connects at a first end 132 to plate 115 and at the other end 134 to housing body 110 by nut 114. Tube 130 is 1.5 inch O.D.×0.049 inch wall, 321 stainless steel. An annulus 136 is defined by an outer surface 138 of tube 118 and an inner surface 140 of housing body 110. The annulus 136 serves to direct a hot hydrogen exterior port 111 toward annulus 124 and out injector assembly 92 (FIG. 4). An annulus 131 is defined by outer surface 138 of tube 118 and inner surface 129 of tube 130 and is filled with insulation 87 that is kept from falling in annulus 136 by a sleeve 133. The reactor tube 98 (FIG. 3) is 1.5 inch O.D.×0.049 inch wall (Dimension "B", 321 stainless steel tube, is 3 feet long (Dimension "A"), and is connected to the housing body 110 by nut 116. The overall injector assembly 92 is about 1 ft long (Dimension "C").

In operation, the coal liquefaction plant functions in the following manner: A pulverized bituminous coal such as Kentucky hvAb may be utilized. Other types of pulverized coal such as lignite and sub-bituminous may also be used. The coal is typically 70% less than 74 microns in size (200 mesh coal) and is fed into high pressure coal feeder 16. The average coal particle size is 40 to 50 microns. A quarter inch line approximately 20 feet long directs dense phase coal from valve 34 into post tube 120 outside of top flange 37 towards the injector assembly 92. The pressure shells 41 and 53 are pressurized with nitrogen to approximately 1000 psig from nitrogen supply system 12. Typically, a 70 psi differential between coal feeder 16 and the pressure shells 41 and 53 is maintained to encourage coal flow in a dense phase through feed line 36 into the injector assembly 92. In other words, the pressure within the coal feeder is approximately 1070 psig during operation. In this specific example hydrogen from hydrogen source 48 is directed towards the coal feeder 16 through hydrogen feed line 30 and the ratio of hydrogen to coal is about 0.005 lbs of hydrogen per pound of coal. Obviously, an inert gas may be utilized in place of the hydrogen with the pulverized coal from inert gas source 50 to the coal feeder 16. Hydrogen is additionally fed from hydrogen source 48 through a conduit 29 into the hydrogen preheater assembly 39. The hydrogen is directed into a 321 stainless steel preheater coil 43 at end 45. The coil 43 at end 45 is ¼ inch O.D.×0.035 inch wall and as the helix progresses down the coil 43 it transitions into a 5/16 inch O.D.×0.049 inch wall coil and from there into a ⅜ inch O.D.×0.083 inch wall coil. The hydrogen exits coil 43 at end 47 towards coiled tube 100 which directs hot hydrogen into the injector assembly 92. The hydrogen flowrate is 10 to 50 percent of the flowrate of dense phase coal. The coil is about 260 inches long in this example. The hydrogen is typically fed into coil 43 at the rate of 0.025 lbs per second. At startup the dense phase coal is flowed through feed line 36 into the post tube 120 outside top flange 37 and into the injector assembly 92 followed by introduction of hot hydrogen through the preheater coil 43. The hydrogen exits the heated coil in a temperature range between 1500° and 2000° F. (a typical temperature is 1650° F.) adjacent the injector assembly 92. Typically, in the foregoing example the reaction temperature within the chamber by reactor tube 98 is found to be about 1100° F. with a residence time of the pulverized coal within the reactor tube 98 of about 150 milliseconds when the hot hydrogen flowrate is 0.36 lbs of hydrogen per pound of coal. The reaction time in reactor tube 98 may be between 10 and 500 milliseconds for the hydrogenation process. As can be seen from the above, with a typical reaction temperature of about 1100° F. and a hydrogen temperature range of 1500°–2000° F., the hydrogen temperature is from 400° to 900° F. in excess of the typical reaction temperature.

It is desirable to promote better mixing to assure that hot hydrogen moves past the coal particles within the reactor tube 98. For example, the hot hydrogen velocity exiting the injector assembly 92 is approximately 1000 ft/second while the velocity of the dense phase entrained coal exiting the injector is about 7 ft/second. Within these parameters approximately 19 to 20% of the coal carbon is converted into a synthetic crude oil having a boiling range of about 200°–350° C. and a heating value of 15,800 BTU per lb, 9% to gas containing methane, ethane, and carbon oxides, and about 3% to organic compounds in the quench water. The coal throughput rate is approximately 33,000 lbs per hour ft$^2$ reactor cross-section or 11,000 lbs per hour ft$^3$ reactor volume. The products of reaction are rapidly quenched to about 225° F. downstream of exit plane 99 of reactor tube 98 in a distance of about 1 ft, the reaction products passing by water spray nozzles 106 in the quench zone below the reaction chamber defined by reactor tube 98. The water flowrate through the multiplicity of water spray nozzles is from 2 to 6 gallons per minute. The products are then moved into the catch tank 52 and from there to the various drums 78 where the solids are collected the gas and by-products being directed into separator tank 56 and the by-products being directed through burnstack 58.

It would be obvious to use other means to heat the hydrogen being separately directed to the injector assembly 92 other than use of high electrical current to heat up a coil which is transporting the hydrogen. For example, a conventional fuel fired furnace or heater could be utilized to heat up a coil tube containing hot hydrogen. Many other methods to heat hot hydrogen are within the state of the art.

Turning now to FIG. 6 an alternative reactor tube 141 is illustrated wherein one end of the reaction chamber connected to the injector assembly 92 at end 142 begins a diverging wall section which diverges towards end 144 adjacent plate 146. The diverging walls defining a reaction chamber 150 tend to discourage sticking of the partially hydrogenated products passing through the reactor tube 141, thus minimizing any tendency to plug.

FIGS. 7 and 8 disclose a different type of injector commonly known in the rocket engine field as a four-on-one injector. The injector consists of a center post 154 which transports dense phase coal particles and is supported within an upper plate 156 and a bottom injector plate 160. The inner face 157 of plate 156 and the inner face 158 of injector plate 160 define an annular chamber 162 which directs hot hydrogen entering a conduit 164 from the preheater assembly into the chamber. A thermal insulator 159 is provided around the center post 154 so that coal particles transported within center post 154 are not prematurely heated. The injector plate 160 has drilled therein a series of four orifices 166 equidistantly spaced around the injector (FIG. 8) each of the orifices having an impingement angle with respect to the center line of the center post 154 of approximately 30° which facilitates greater mixing of the minute coal particles exiting center post 154 with the impingeing hot hydrogen downstream of the injector face. FIG. 8 better depicts the relationship of the orifices with respect to the center post 154.

It would be obvious to configure any number of gas streams on the central coal stream with different impingement angles, all of which are well within the state-of-the-art particularly in the rocket engine field.

It will, of course, be realized that various modifications can be made in the design and operation of the present invention without departing from the spirit thereof. Thus, while the principle preferred construction and mode of operation of the invention have been explained and what is now considered to represent its best embodiment has been illustrated and described, it should be understood that within the scope of the appended claims, the invention may be practiced otherwise than as specifically illustrated and described.

We claim:

1. An apparatus for reacting a carbonaceous material with hydrogen to produce hydrocarbon liquids and gases which comprises:
   means for flowing a pulverized carbonaceous material entrained in a gas in a dense phase in a flow conduit toward an injector adjacent to a reaction chamber, said reaction chamber adjacent to said injector comprising an elongated tube having first and second ends, said tube connected at said first end to said injector,
   means for flowing a separate source of hydrogen in another conduit toward said injector adjacent said reaction chamber, said conduit comprising a heat conductive coil helix having an upstream end and a downstream end, the inside diameter formed by the walls of said conduit of said upstream end being smaller than the inside diameter of said downstream end, whereby the gradually increasing inside diameter of said conductive conduit from said upstream end to said downstream end facilitates the flow of hydrogen as it is heated, expanded and accelerated down said heated conduit,
   electrical heating means for heating said source of hydrogen,
   means for injecting said dense phase pulverized coal through said injector into said reaction chamber,
   means for injecting said heated source of hydrogen through said injector into said reaction chamber,
   means for injecting said heated source of hydrogen through said injector into said reaction chamber and insulation means to thermally separate said pulverized carbonaceous material and said hydrogen prior to their injection into said reaction chamber to prevent premature reaction of said pulverized carbonaceous material,
   means for quenching reaction products exiting said second end of said reaction chamber to rapidly arrest said reaction at a predetermined time period when reaction products exit said reaction chamber, and
   means for collecting said reaction products.

2. The invention as set forth in claim 1 further comprising flow control means for maintaining said separate flow of heated hydrogen at a flow rate of about 10 to 50 percent of the flow rate of said dense phase coal.

3. The invention as set forth in claim 1 wherein said electrical heating means includes means for maintaining direct current electrical energy at an amperage rate of between 600 and 800 amps.

* * * * *

UNITED STATES PATENT AND TRADEMARK OFFICE
CERTIFICATE OF CORRECTION

PATENT NO. : 4,169,128

DATED : Sep. 25, 1979

INVENTOR(S) : Jerry E. Sinor et al

It is certified that error appears in the above-identified patent and that said Letters Patent is hereby corrected as shown below:

Front page under [63], "Apr. 24" should read --May 24--.

Column 7, line 3, "feed" should read --feeder--.

Column 8, line 33 after "reactor" insert --tube--.

Column 10, line 45 after "collected" insert --,--(comma).

Signed and Sealed this

Fifth Day of June 1984

[SEAL]

*Attest:*

GERALD J. MOSSINGHOFF

*Attesting Officer*    *Commissioner of Patents and Trademarks*